(12) United States Patent
Hietala et al.

(10) Patent No.: US 6,257,048 B1
(45) Date of Patent: Jul. 10, 2001

(54) METHOD AND APPARATUS FOR MEASURING SURFACE CHANGES, IN POROUS MATERIALS, USING MULTIPLE DIFFERENTLY-CONFIGURED ACOUSTIC SENSORS

(75) Inventors: Susan Leslie Hietala; Vincent Mark Hietala, both of Placitas; Chris Phillip Tigges, Albuquerque, all of NM (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/335,762

(22) Filed: Jun. 18, 1999

Related U.S. Application Data

(60) Provisional application No. 60/090,237, filed on Jun. 22, 1998.

(51) Int. Cl.[7] .................................................. G01N 29/20
(52) U.S. Cl. ...................... 73/24.01; 73/24.03; 73/24.06; 73/597
(58) Field of Search .............................. 73/597, 602, 609, 73/24.01, 24.03, 24.06, 643; 310/313 R

(56) References Cited

U.S. PATENT DOCUMENTS

| | | | | |
|---|---|---|---|---|
| 3,840,825 | * | 10/1974 | Gerard | 310/313 R |
| 4,312,228 | * | 1/1982 | Wohltjen | 73/597 |
| 5,325,704 | * | 7/1994 | Mariani et al. | 73/24.06 |
| 5,480,554 | | 1/1996 | Degen et al. | |
| 5,576,480 | | 11/1996 | Hopkins et al. | |
| 5,640,236 | | 6/1997 | Nagashima . | |

OTHER PUBLICATIONS

Stetter, J.R. Sensors and Actuators B1, 1990, 43–47.*

* cited by examiner

Primary Examiner—Hezron Williams
Assistant Examiner—Michael Cygan
(74) Attorney, Agent, or Firm—Dickson G. Kehl; Virginia B. Caress; Paul A. Gottlieb

(57) ABSTRACT

A method and apparatus for measuring surface changes, such as mass uptake at various pressures, in a thin-film material, in particular porous membranes, using multiple differently-configured acoustic sensors.

23 Claims, 4 Drawing Sheets

METHOD AND APPARATUS FOR MEASURING SURFACE CHANGES, IN POROUS MATERIALS, USING MULTIPLE DIFFERENTLY-CONFIGURED ACOUSTIC SENSORS

This application claims benefit of provisional 60/090,237 filed Jun. 22, 1998.

GOVERNMENT RIGHTS

The United States Government has rights in this invention pursuant to Contract No. DE-AC0494AL85000 between the U.S. Department of Energy (DOE) and Sandia Corporation.

FIELD OF THE INVENTION

The present invention pertains to a method and apparatus for measuring surface changes, such as stiffness (effective modulus) and mass uptake, in a thin-film porous material, using multiple differently-configured acoustic sensors, thereby to characterize the material. More particularly, the invention is a method and apparatus for measuring gas adsorption at various relative pressures. Still further, it is a method and apparatus for decoupling effects, such as of shear modulus and mass, when taking measurements on thin-film devices.

BACKGROUND OF THE INVENTION

Characterization of microporous materials in terms of surface areas, pore sizes and pore size distributions, is a challenging area of research. The need for improved thin film characterization techniques has become increasingly important for understanding the effects of synthesis techniques as well as the ability to describe the porous properties of membranes and chemical sensors.

Micropores are a unique class of pores which, due to their atomic sizes, have unusual properties. This small size makes microporous materials notoriously difficult to characterize. However, this small size also makes these materials enormously useful for various applications such as gas separation membranes.

Methods to characterize microporous materials have not kept up with the surge in research to produce microporous membranes. The research of thin film properties has always been elusive, especially in the area of microporous materials, since the sensitivity of instrumentation is not conducive to measuring the volume properties of the small pores.

Characterization of thin-film properties is important to industries involved in research or development of membranes, optical coatings, barrier coatings for semiconductors, barrier coatings for preservation, and other thin film technologies where porous microstructure affects the performance characteristics of the materials.

The varied uses of porous materials, have led to a myriad of classifications. Some are based on a physical dimension of the pores, while others are based on the separation properties. The IUPAC (International Union of Pure and Applied Chemists) pore size designations, shown below, will be used herein:

pores of diameter <20 Å are considered micropores;
pores of diameter >20 Å and <500 Å are considered mesopores; and
pores of diameter >500 Å are considered macropores.

Although the prior art has exploded with references to microporous thin films, there still remain relatively few techniques to characterize these films. The most popular are permeability, ellipsometry and gas adsorption.

The most common technique to characterize microporous membranes involves measuring gas permeability through a supported membrane. In a variation of the permeability technique, a microporous membrane is equilibrated with known pressure of a condensable vapor, and the permeability coefficient of an incondensable gas through the membrane is measured. A significant drawback to this technique is that is may take weeks or months to obtain sufficient data to calculate pore size distribution, due to equilibration times.

Ellipsometry is commonly used in conjunction with other characterization techniques to gather complementary data such as film thickness. In one technique, the pores are initially filled with adsorbates of various sizes to obtain a total pore volume. Then the films are equilibrated at some relative pressure (in flowing gas), and the pore volumes are determined using the Lorentz-Lorenz relation. Unfortunately, the calculations are only approximate, since the Lorentz-Lorenz relation used does not include the effects of shape anisotropy on the index, or quantum mechanical effects which may be present for structures of near-atomic dimensions. Additionally, reproducible results were only obtained on hydroxylated surfaces and hydroxillation took from several hours to days to achieve.

Gas adsorption techniques have been extensively used for surface area and pore size analysis of materials. One of the limitations of this technique is that the surface area/pore volume of the material must be large enough for the sensitivity of the instrument, which for commercially available instruments (e.g., Micromeritics ASAP 2000) is typically a surface area of >10 $m^2$. Adaptions of bulk instrumentation have been attempted to increase this range. In general, this is not enough sensitivity to probe thin films. For example, microporous silicates may have nitrogen surface area as low 1 $m^2/g$ in bulk form. For a typical 1 $\mu m$ film of 10% accessible porosity, a film area of >100 $cm^2$ would be required for standard analysis. Nonetheless, bulk methods have been attempted to characterize porous films, and only illustrate the need for reliable thin film characterization. The results showed an array of inconsistent differences between surface areas and pore radii of the bulk and supported sample, with the bulk values often higher.

There is a need for a method for overcoming the inherent limitations of existing measurement methods. The present invention provides the use of more than one acoustic sensor, each acoustic sensor being differently configured. Using this technique, the contribution of the shear modulus of the sensor itself can be ascertained and the measurement corrected accordingly.

OBJECTS AND SUMMARY OF THE INVENTION

Accordingly, it is an object of the present invention to provide a method and apparatus for determining the characteristics of a thin-film material from adsorption isotherm by use of multiple acoustic sensors, each of which is configured differently from any other one.

It is another object of the invention to be able to quickly and accurately determine key design parameters of a thin-film material in a matter of hours or days versus months, as is necessary with existing and traditional methods.

It is further object of the invention to be able to take timely measurements under a wide range of environmental conditions, such as temperature ranges from cryogenic to in excess of 400° C., and/or pressures from vacuum to in excess of 40 psig, as well as under vacuum conditions.

It is yet another object of the invention to be able to take measurements under dose conditions as well as the more traditional flow conditions.

It is an additional object of the invention to be able to take measurements on porous materials, in particular microporous thin-film membranes, i.e., those with pore sizes less than 20 Å.

In summary, the present invention provides a method and apparatus for characterizing a porous material, particularly a thin-film material, by measuring the mass of adsorbent, e.g., gas, in the material at various pressures. The present invention comprises: providing first and second acoustic sensors, such as Surface Acoustic Wave (SAW) sensors, each having different operating characteristics to provide different responses, for instance, frequency or other appropriate responses, to identical inputs such that contributions of mass and effective modulus of the material to the frequency, or other appropriate, responses of the sensors are separated, applying identical materials, for example thin-film materials, on a chosen surface of each of the first and second acoustic sensors; placing the first and second acoustic sensors in an appropriate environment for measurement, such as a chamber, providing an adsorbate, such as gas, into the environment at various pressures and measuring the responses of the first and second acoustic sensors at each pressure, and calculating the mass of adsorbate adsorbed in the material based on these responses.

These and other objects of the present invention will become apparent from the following detailed description.

DETAILED DESCRIPTION OF THE INVENTION

Adsorption, for example gas adsorption, is enormously useful in the probing of porous properties of materials. The general idea is to put a known amount of molecules of known size onto a surface. From this data, the surface can be characterized in terms of surface areas, pores sizes and pore size distributions, etc., which are calculated using a variety of known techniques.

The term adsorption connotes the condensation of gases onto a surface, as opposed to into a surface (absorption). This term is now used generally to describe both adsorption and desorption. The adsorbate (or adsorbent) refers to the material actually being adsorbed onto the solid surface.

Acoustic devices, for example Surface Acoustic Wave (SAW) devices, have been used as chemical and physical sensors. Continuing to use the mechanics of a SAW device as the example, a surface acoustic wave is described as a wave traveling across a surface, where the atoms and their center of mass move together, as in long wavelength acoustical vibrations. The easiest and most common mode of surface wave to excite is called the Rayleigh wave. For this wave, >95% of the energy is confused within a depth equal to $(2\pi)^{-1}$ times one acoustic wavelength, which for quartz oscillating at 100 MHz is about 5 μm. Surface acoustic waves are efficiently generated using piezoelectrics.

It should be noted that, although gas adsorption has been used to describe the operation of the invention herein, acoustic devices, such as will be described for use in the invention, are capable of operation in ambient conditions, and can be used to identify the adsorbate, rather than just characterizing the film using an ad sorbate. The technology of the present invention can be used in either capacity, and the present invention is intended to encompass both uses.

Acoustic devices have inherent advantages over traditional Quartz-Crystal Microbalances (QCM) for use as sensors in testing thin-film porous membranes. In particular, microporous membranes (those with pore diameter less than 20 Å), are a challenge to test using conventionally accepted methods. If the material, e.g., a thin-film membrane, to be tested is of significantly smaller thickness than the sensor to be used for the test, the mass and, more significantly, the shear modulus (stiffness) of the sensor can noticeably bias the measurement. This is true even when the sensors are used in "matched pairs". In addition, conditions of testing, including temperature extremes, pressure, vacuum, humidity, and other environmental factors such as mechanical vibration, dictate the need of robust acoustic sensors.

Figure 1:
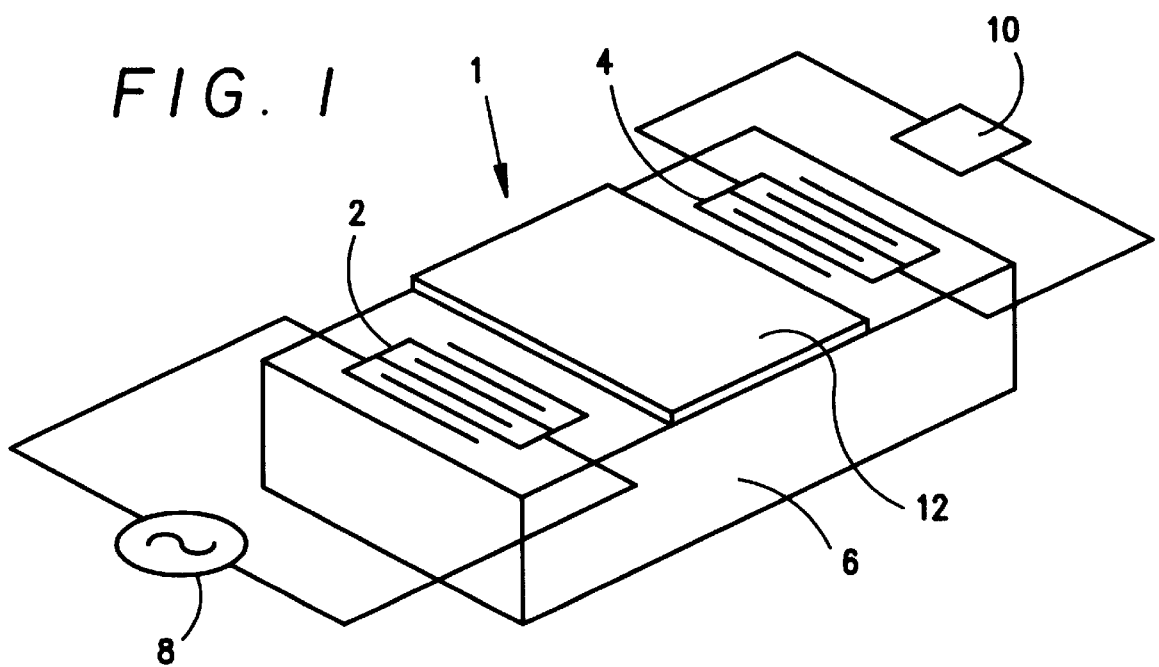
FIG. 1 is a schematic perspective view of an acoustic sensor covered with a thin-film material.

FIG. 1 is a schematic perspective view of an acoustic sensor covered with a thin-film material. Referring to FIG. 1, an acoustic sensor 1 is disclosed, comprising interdigital transducers 2 and 4, placed on a piezoelectric substrate 6. For purposes of having an example with which to describe the structure shown in FIG. 1 and its associated mathematics, sensor 1 is chosen to be a SAW sensor, although a variety of types of acoustic sensors may be used in the subject invention. RF signal generator 8 is operably connected to transducer 2, launching a surface acoustic wave which propagates across the substrate. Transducer 4 receives the acoustic wave and converts it back into an electrical signal, which is processed by a frequency counter 10. A thin-film material 12, which is being characterized by the measurement, is disposed on a chosen surfaces of sensor 1. For the purpose of describing the present invention using the Figures herein, the chosen surface is taken to be a top surface.

The mechanical wave makes sensor 1 quite sensitive to surface loading, such as the thin-film material 12. Sensitivities exceeding 10 picograms/cm$^2$ are possible. For example, in a gas adsorption arrangement using nitrogen as the adsorbate, this is equivalent to $2.15 \times 10^{11}$ molecules/cm$^2$ (or 0.035% surface coverage based on area of nitrogen molecule) which allows for gas adsorption to be possible on very low volume thin films. Additionally, when the sensor is in an oscillation loop, the frequency of oscillation critically depends on the sensor delay (of phase shift). With modern instrumentation, the frequency (or time) can be measured with an almost unlimited accuracy (one part in $10^9$ at 100 MHz is trivial) and therefore incredible sensitivities are attainable.

The FIG. 1 sensor is sensitive to a variety of mechanical influences. Of interest in the present invention are mass loading ($\Delta m = \Delta ph$), thin film effective modulus change ($\Delta S \approx \frac{1}{4}(\Delta Eh)$), stress and surface tension changes ($\Delta y \approx \Delta \sigma h$) and temperature changes ($\Delta T$).

These contributions to the time delay of an acoustic sensor (still using a SAW sensor as the example) in an oscillating loop can be written in general terms as:

$$\frac{\Delta V_R}{V_{R_O}} = \frac{\Delta F}{f_o} = -\frac{\Delta \beta_R}{\beta_{R_O}} = -\frac{\Delta E_R}{E_{R_O}} = -k_m \frac{\Delta m}{m_o} + \quad (1)$$
$$k_s \frac{\Delta S}{S_o} + k_\sigma \frac{\Delta \sigma_Q}{\sigma_{Q_o}} + k_\gamma \frac{\Delta \gamma}{\gamma_o} - k_T \frac{\Delta T}{T_o}$$

where:

During gas adsorption measurements, the objective is generally to measure the mass uptake at various relative pressures to calculate the porous properties of the thin film from standard analytical techniques. In order to measure the mass uptake accurately, it is necessary to minimize or account for other contributions to the frequency response. To minimize temperature effects, measurements are performed isothermally, and sensor materials are chosen with "turnover temperatures" near that of the operation temperature. The stress term is minimized by using a thick Quartz sensor, which minimizes the increase or decrease of the path length between the transducers. Due to the thickness of the Quartz, the stress and surface tension effects on the sensor response are minimized.

It should be particularly noted, in connection with Equation (1), that frequency response, i.e., change, is equivalent to the velocity change, and the negative of the phase change, and the negative of the energy change. Therefore, in using the present invention, measurement of any of these is equivalent to the information obtained by measuring the frequency change. Thus, while the invention is described in terms of measuring frequency response, the invention is intended to encompass the measurement of other appropriate responses.

The main contribution of the sensor response to adsorption on a microporous film are the mass and effective modulus terms. These effects are coupled, primarily due to the small diameter of the micropore.

For a Rayleigh surface wave, the normalized frequency shift is:

$$\frac{\Delta f}{f_o} = k\left[-\frac{V_R}{4}\left(\frac{|V_{Ry}|^2}{P_R} + \frac{|V_{Rz}|^2}{P_R}\right)h\rho' + \left(h\mu' \frac{\lambda' + \mu'}{\lambda' + 2\mu'}\right)\left(\frac{1}{V_R} \frac{|V_{Rz}|^2}{P_R}\right)\right] \quad (2)$$

where:
 f=the frequency of oscillation
 $V_R$=velocity of Rayleigh mode acoustic wave
 h=thickness of the thin-film isotropic overlay
 p'=density of the thin-film isotropic overlay
 $\mu'$=the shear modulus of the thin-film isotropic overlay
 $\lambda'$=the bulk modulus of the thin-film isotropic overlay
 $P_R$=the acoustic power
 $V_{Ry,z}$=surface particle displacement velocity along the y or z axis
 k=the ratio of effective sensor coverage
and the subscript "o" refers to the initial conditions of the unloaded sensor, and "$\Delta$" indicates the difference between the current and initial conditions (i.e., $\Delta f=f-f_o$). The equation is derived using perturbation theory to describe the expected change to mass and effective shear modulus due to change in resonant frequency of an acoustic, e.g., a SAW, sensor (in a delay loop oscillator loaded with a lossless isotropic thin film).

From equation (1), $$\frac{\Delta V_R}{V_{R_O}} = \frac{\Delta f}{f_o} = \frac{\Delta \beta_R}{\beta_{R_O}} = -\frac{\Delta E_R}{E_{R_O}} \quad (3)$$

In large pore materials, such as mesopores, the shear modulus term in adsorption experiments can be neglected, but in small pore films, such as micropores (<20 Å), the contribution of the shear modulus to the frequency shift is significant. To address this contribution, the use of two (or more) differently configured acoustic sensors (as discussed below) permits determination of each sensor's contribution and subsequent adjustment of the readings.

Figure 2:
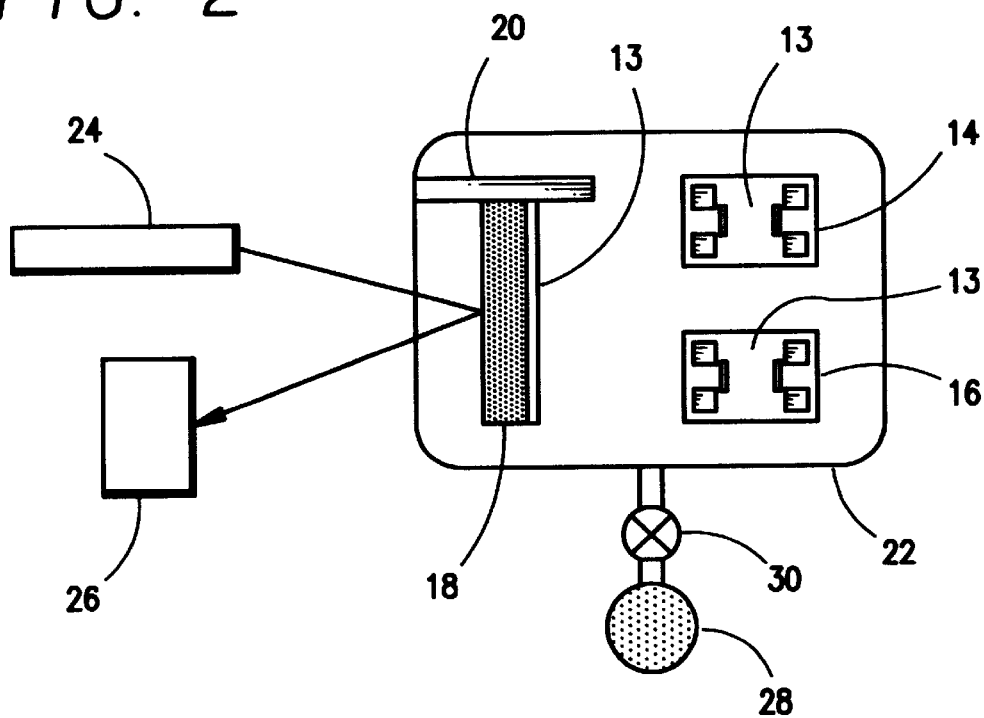
FIG. 2 is a schematic representation of an apparatus using dual acoustic sensors coated with the thin-film material.

FIG. 2 is a schematic representation of an apparatus for simultaneous measurement of beam bending due to strain induced by gas adsorption in a thin-film material and mass uptake of the thin film from the frequency responses of dual acoustic sensors coated with the thin film. Referring to FIG. 2, identical thin-films 13 are disposed on respective top surfaces of two acoustic sensors, here using the examples of a Quartz SAW sensor 14, a GaAs SAW sensor 16 (the thin-film is shown previously in FIG. 1) and a silicone wafer 18, which is configured as a cantilevered beam secured at a supporting member 20.

While a Quartz SAW sensor and a GaAs SAW sensor are used as examples for the purpose of describing the dual sensor structure of FIG. 2, the present invention only requires that the sensor material be piezoelectric material or material having piezoelectric properties. There are a myriad of crystal types that could be substituted for either the Quartz or the GaAs, which would be equally successful in the present invention. For example, there are 21 noncentrosymmetric space groups which lead to piezoelectric properties. More specifically, a crystal such as lithium niobate may be used. The piezoelectric materials to be used in the sensors are chosen to provide complementary information. The present invention, as shown in FIG. 2, is directed to the use of more than one (specifically two) sensors of different material or material properties and is not limited by the use of specific materials.

Figure 5:
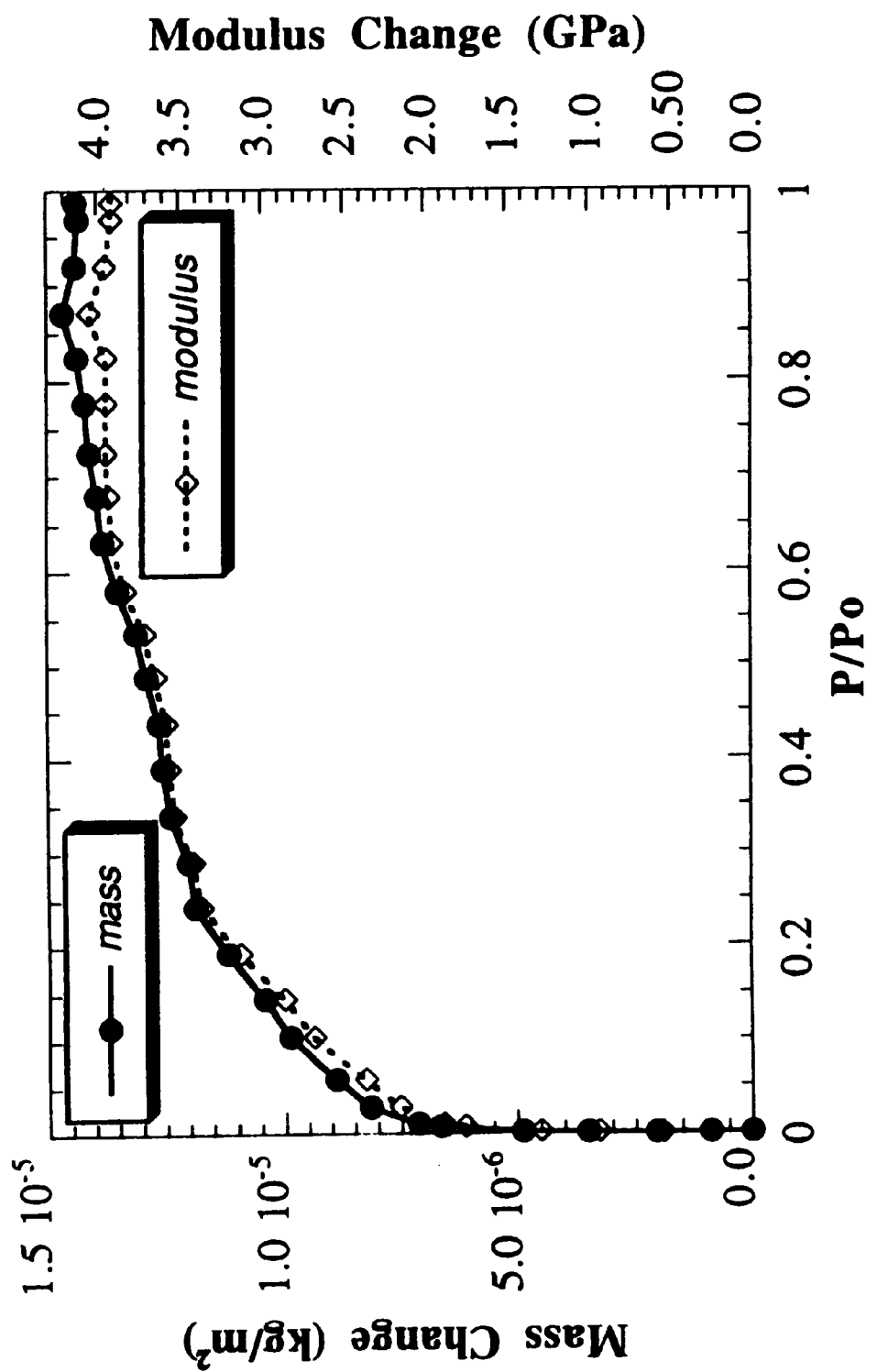
FIG. 5 depicts the mass and effective shear modulus contribution to the adsorption of methanol on a thin-film.

The thin-film is a sol-gel derived microporous A2 silica film. The A2 silica system was chosen for this example because of its microporous properties, the general expertise in the laboratory for synthesizing the sol and forming thin films, and because the films are isotropic, a pre-requisite for use of Auld's perturbation equation (B. A. Auld, *Acoustic Fields and Waves in Solids*, Vol. II, John Wiley & Sons, New York (1973)). The sensors 14 and 16 and the silicone wafer 18 are placed in an appropriate measurement environment, here, as an example, vacuum chamber 22. A HeNe laser 24 and a detector 26 are operably configured relative to the silicone wafer 18 to detect its bending due to the strain induced by the adsorption of the gas. The thin films are then allowed to outgas under vacuum overnight (either at room temperature or at elevated temperatures). After outgassing, chamber 22 is dosed with a dry (water removed) sorbate from a supply 28 through a valve 30. The deflection of the silicone wafer 18, as well as the frequency response of the Quartz and GaAs SAW sensors 14 and 16, are recorded as a function of relative pressure, as best shown in FIG. 5 (to be described later). The SAW sensors 14 and 16 are used calculate the mass uptake of the film, but also give an effective modulus change in the film.

Now going back to Equation 2, it should be noted that the first term of Equation (2) depends only on the mass density of the film (hp), whereas the second term depends on the film effective shear modulus, $\mu'$.

Rearranging and defining terms in Equation (2) gives the following equation for a sensor fully covered with a thin-film material:

$$\Delta f = \frac{f_o V_R}{4}(R_y + R_o)\Delta m + \Delta s \frac{f_o}{V_R} R_z \quad (4)$$

where:
$\Delta f$=the frequency shift
$f_o$=the frequency of oscillation of an unloaded sensor
$V_R$=the velocity of the acoustic wave
$R_{y,z} = |V_{Ry,z}|^2 / P_R$=the normalized surface particle velocity
$\Delta m = hp$=the surface mass density $$\Delta s = \Delta\left(h\mu' \frac{\lambda' + \mu'}{\lambda' + 2\mu'}\right) = \text{the effective shear}$$

modulus term (sometimes referred to as the stiffness)

For an isotropic film:

$$\mu' = \frac{E}{2(1+\upsilon)} \quad (5)$$

and $$\lambda' = \frac{E}{3(1-2\upsilon)} \quad (6)$$

Where:
E=Young's modulus
$\mu$=Poisson's ratio

Substituting Eqns. (5) and (6) into $\Delta s$ yields:

$$\Delta s = \Delta\left(h\mu' \frac{\lambda' + \mu'}{\lambda' + 2\mu'}\right) = \Delta\left(E\frac{h}{4} \frac{4\upsilon - 5}{(5\upsilon^2 + \upsilon - 4)}\right) \quad (7)$$

Figure 3:
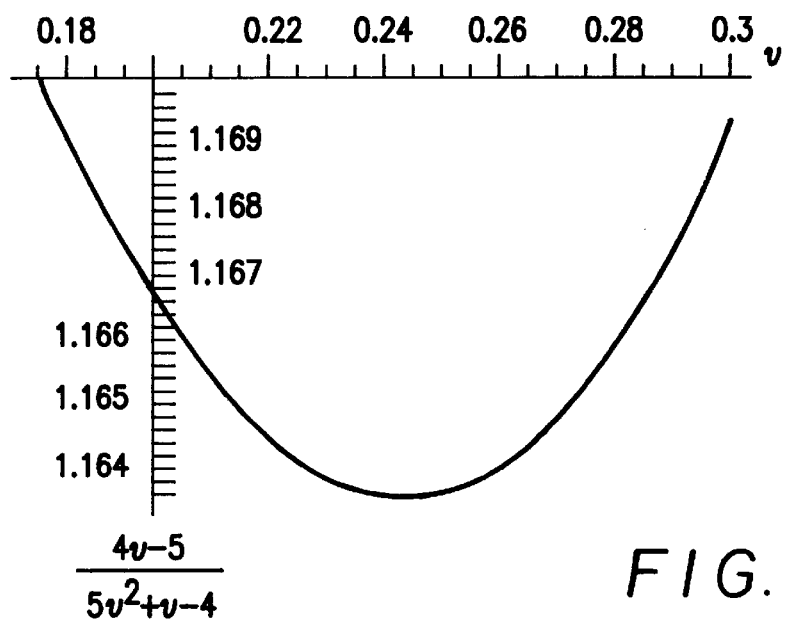
FIG. 3 illustrates a plot of Equation (7) versus Poisson's ratio.

FIG. 3 illustrates a plot of Equation (7) versus Poisson's ratio. For typical Poisson's ratios of silicates (0.2 to 0.3), a plot of the $\mu$ terms in Equation (7) above shows the prefactor values to be approximately constant, as shown in FIG. 3, at a value of approximately 1.16. Therefore, the effective shear modulus is directly proportional to Young's modulus.

For identical films on dual acoustic sensors (see FIG. 2 using the examples of Quartz and GaAs SAW sensors), $\Delta m$ and $\Delta s$ are identical, and Equation (3) becomes:

$$\Delta f_1 = -\frac{f_{o1} V_{R1}}{4}(R_{y1} + R_{z1})\Delta m + \Delta s \frac{f_{o1}}{V_{R1}} R_{z1} \quad (8)$$

and $$\Delta f_2 = -\frac{f_{o2} V_{R2}}{4}(R_{y2} + R_{z2})\Delta m + \Delta s \frac{f_{o2}}{V_{R2}} R_{z2} \quad (9)$$

then $$\begin{bmatrix}\Delta f_1 \\ \Delta f_2\end{bmatrix} = \begin{bmatrix}-\frac{f_{o1}}{4}V_{R1}(R_{y1}+R_{z1}) & \frac{f_{o1}}{V_{R1}}R_{z1} \\ -\frac{f_{o2}}{4}V_{R2}(R_{y2}+R_{z2}) & \frac{f_{o1}}{V_{R2}}R_{z2}\end{bmatrix}\begin{bmatrix}\Delta m \\ \Delta s\end{bmatrix} = S\begin{bmatrix}\Delta m \\ \Delta s\end{bmatrix} \quad (10)$$

Solving for the mass and effective shear modulus changes gives:

$$\begin{bmatrix}\Delta m \\ \Delta s\end{bmatrix} = S^{-1}\begin{bmatrix}\Delta f_1 \\ \Delta f_2\end{bmatrix} \quad (11)$$

The mass and effective shear modulus components may then be found by substituting the known and measured values into Equation (11). It should be particularly noted that the present invention is not limited to the equation set out above. In the practice of the present invention, the equations discussed herein, and most especially this equation, are meant to encompass any equivalent form thereof.

The surface wave velocity, $V_R$, and the normalized mechanical wave displacements, R (described in Equation (4)), at the "free" electrical boundary condition are tabulated in the table below for St-Quartz and GaAs SAW sensors.

| Property | ST Quartz | GaAs |
|---|---|---|
| $V_R$ | 3158 | 2800 |
| $(R_y)^{1/2}$ | $4.2 \times 10^{-6} \omega^{1/2}$ | $1.233 \times 10^{-6} \omega^{1/2}$ |
| $(R_z)^{1/2}$ | 97 | 100 |

The units for $V_R$ str m/s, units for $(R_z)^{1/2}$ are $$\frac{\frac{m}{s}}{\left(\frac{W}{m}\right)^{1/2}}$$

and the units for $f_n$ are MHz.

The equations are used to calculate the mass and effective shear modulus changes from the frequency change of the Quartz and GaAs sensors which are obtained by substituting the values from the table above into Equation (10).

$$S = \begin{bmatrix} -\frac{f_{oQ}}{4}V_{RQ}(R_{yQ}+R_{zQ}) & \frac{f_{oQ}}{V_{RQ}}R_{zQ} \\ -\frac{f_{oGa/1s}}{4}V_{RGa/1s}(R_{yGa/1s}+R_{zGa/1s}) & \frac{f_{oGa/1s}}{V_{RGa/1s}}R_{zGa/1s} \end{bmatrix} \quad (12)$$

$$= \begin{bmatrix} -1.19 \times 10^9 m^2/kgs & 146.8(m.Pa/s) \\ -8.32 \times 10^8 m^2/kgs & 390.62(m.Pa/s) \end{bmatrix} \quad (13)$$

Inverting Equation (13) yields:

$$\begin{bmatrix}\Delta m \\ \Delta s\end{bmatrix} = \begin{bmatrix} -1.141 \times 10^9 kgs/m^2 & 4.288 \times 10^{-10} kgs/m^2 \\ -0.00243 s/m.Pa & 0.00347 s/m.Pa \end{bmatrix}\begin{bmatrix}\Delta f_Q \\ \Delta f_{GaAs}\end{bmatrix} \quad (14)$$

Figure 4:
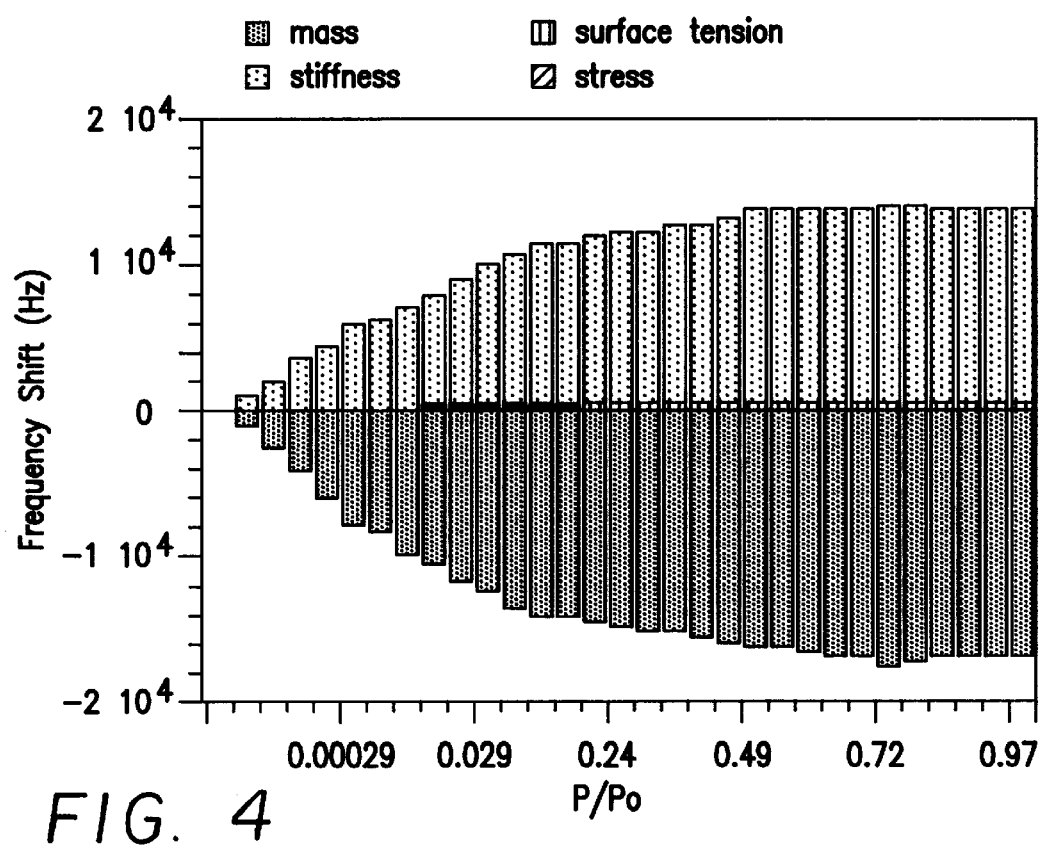
FIG. 4 shows the frequency response of a Quartz SAW sensor during adsorption on thin-film.

The relative responses of the frequency shift due to the mass, effective shear modulus, surface tension and stress are shown in FIGS. 4 and 5. FIG. 4 shows the frequency response of a Quartz SAW sensor due to mass, effective modulus, surface tension, and stress effects during MeOH adsorption on an A2 silica film. FIG. 5 depicts the mass and effective shear modulus contribution to the adsorption of methanol on A2 film, as calculated from the Quartz and GaAs SAW frequency response by Equation (14). Note the quite small contributions (almost undetectable on the scale of the graphs) to frequency shift due to surface tension and stress.

Calculations of the contribution of mass, effective shear modulus, surface tension and stress to the SAW response are possible due to simultaneous collection of complementary adsorption data. The dual sensor technique allows the separation of mass and effective shear modulus contributions, while beam-bending measurement (see FIG. 2) gives an independent measurement of stress, which is used to calculate the stress and surface tension contribution to the SAW response. From the induced strain, the solvation forces in the pores can be calculated. The beam-bending technique can also be used for size exclusion measurements, noting that there is no strain induced in the silicon wafer if the adsorbate does not penetrate into the pores.

A prediction of the variance of the derived quantities, $\Delta s$ and $\Delta m$ (effective shear modulus and mass), can be calculated in terms of the variances of the measured data, $\Delta f_1$ and $\Delta f_2$ to determine the uniqueness of the sensors.

For the dual sensor case (see FIG. 2), rewriting Equation (11) to pull out the frequency dependence from the transfer matrix, the derived quantities, $\Delta s$ and $\Delta m$, are related to the measured quantities, $\Delta f_1$ and $\Delta f_2$, by $$\begin{bmatrix} \Delta m \\ \Delta s \end{bmatrix} = C \begin{bmatrix} \frac{\Delta f_1}{(f_{10} + \Delta f_1)^2} \\ \frac{\Delta f_2}{(f_{20} + \Delta f_2)^2} \end{bmatrix} \quad (15)$$

in which $f_{10}$ and $f_{20}$ are the equilibrium measurement frequencies C is:

$$C = \begin{bmatrix} C_{11} & C_{12} \\ C_{21} & C_{22} \end{bmatrix} \quad (16)$$

$$= \begin{bmatrix} \frac{-2K_{z2}^2 V_{R1}}{D} & \frac{2K_{z1}^2 V_{R2}}{D} \\ \frac{-(K_{y2}^2 + K_{z2}^2)V_{R1}V_{R2}^2}{D} & \frac{(K_{y1}^2 + K_{z1}^2)V_{R1}^2 V_{R2}}{D} \end{bmatrix}$$

where $$D = \pi(K_{y1}^2 K_{z2}^2 V_{R1}^2 + K_{z1}^2(K_{z2}^2(V_{R1}^2 - V_{R2}^2) - K_{y2}^2 V_{R2}^2)) \quad (17)$$

and $K_{yi}$ and $K_{zi}$ are the numerical prefactors of the normalized surface particle velocity of the ith material comprising the first sensor and second sensor (for the examples of the ST-Quartz and GaAs SAW sensors). The final result is:

$$\sigma_{\Delta m}^2 = \frac{C_{11}^2}{f_{10}^4}\sigma_{\Delta f1}^2 + \frac{C_{12}^2}{f_{20}^4}\sigma_{\Delta f2}^2 \quad (18)$$

In a similar fashion, the effective shear modulus part is:

$$\sigma_{\Delta s}^2 = \frac{C_{21}^2}{f_{10}^4}\sigma_{\Delta f1}^2 + \frac{C_{22}^2}{f_{20}^4}\sigma_{\Delta f2}^2 \quad (19)$$

and means that the variance of the sum of independent random variables equals the sum of the variances of these variables.

Figure 6:
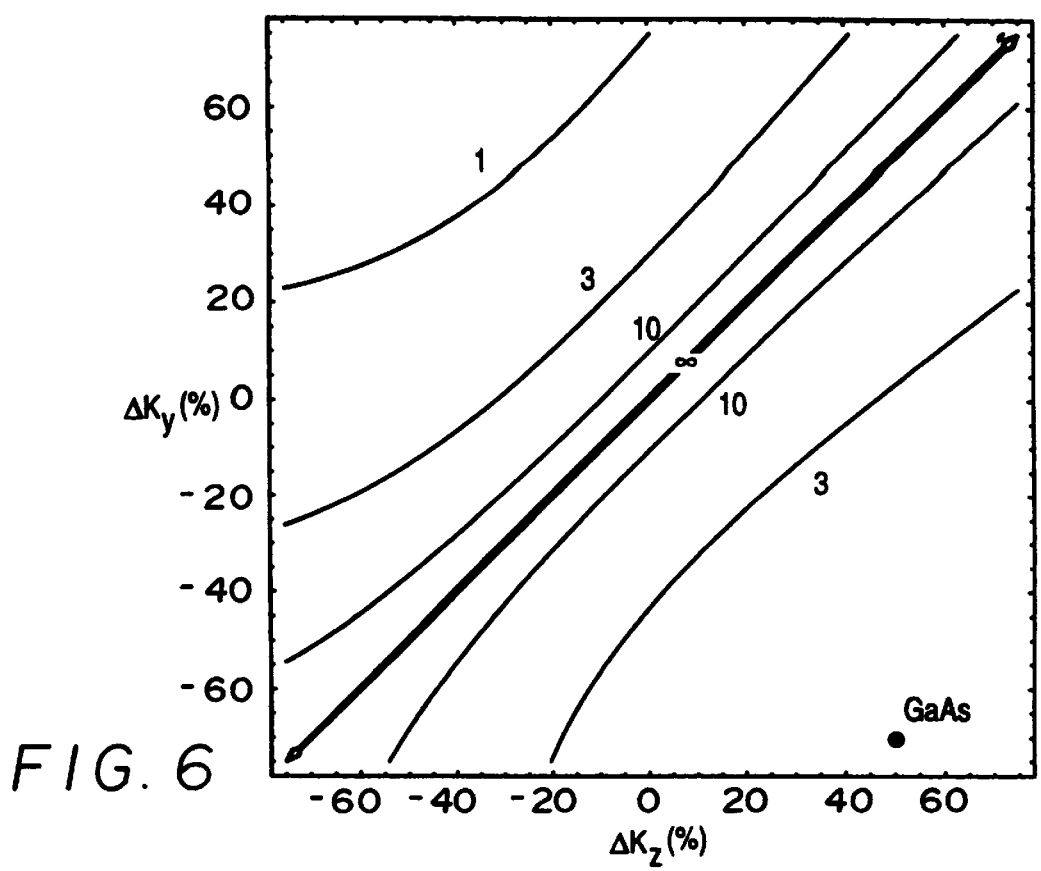
FIG. 6 is a contour plot of normalized mass standard deviation of the GaAs material.
Figure 7:
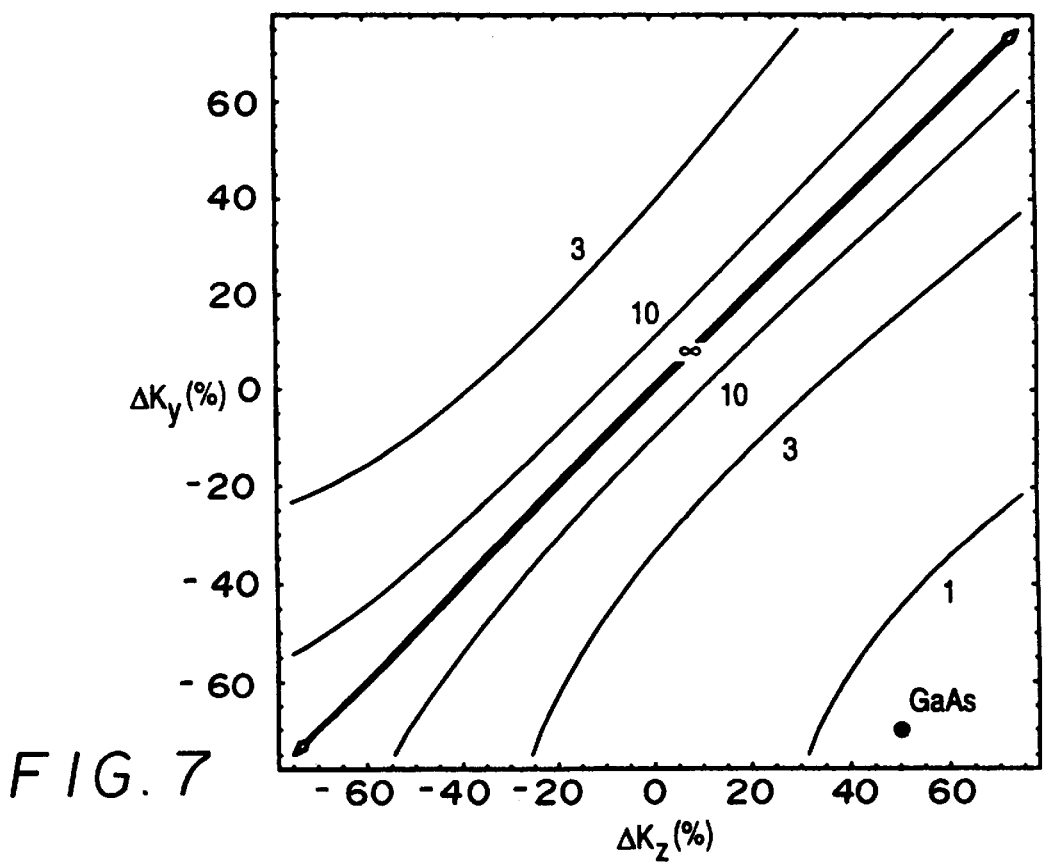
FIG. 7 is a contour plot of the normalized effective shear modulus standard deviation of the GaAs material.

Using the material properties for ST-cut Quartz for material one and setting the material parameters of the second sensor to a percentage variation from the first, contour plots of mass and effective shear modulus normalized standard deviations were generated, as best shown in FIGS. 6 and 7. FIG. 6 describes a contour plot of the normalized mass standard deviation, $\sigma_m$ versus percentage change of $K_y$ and $K_z$ of the second sensor's material. (The first material is Quartz). GaAs is shown at the 1.46 contour. FIG. 7 describes a contour plot of the normalized effective shear modulus standard deviation, $\sigma_m$ versus percentage change of $K_y$ and $K_z$ of the second sensor's material. (The first material is Quartz). GaAs is shown at the 0.65 contour. These plots are normalized to the performance of ST-cut Quartz. The standard deviation of the measured frequencies was assumed to be 1 Hz which is appropriate for the +/− one count error of a frequency contour operating at a 1 second gate (typical in this work). The equilibrium operating frequencies were selected to be $f_{10}=f_{20}=-97$ MHz, and both acoustic wave velocities were set to $V_{R1}=V_{R2}=3158$ m/s, both which are appropriate for Quartz and approximate for GaAs SAWs. In these plots, the standard deviation result approaches infinity when both sensors are identical, or when the velocity coefficients are scaled proportionally (along the diagonal line). Then, with several tens of percent differences in opposite directions, the standard deviation of both of the measurements is seen to rapidly approach, and even surpass, the intrinsic sensitivities of the Quartz sensor.

For a second sensor of GaAs, the particle velocity coefficients are found to be $K_y=1.23\times10^{-6}$ and $K_z=4.172\times10^{-6}$. These represent a −70% change in $K_y$ and a +49% change in $K_z$ as shown in FIGS. 5 and 6. The resulting normalized standard deviation relations are:

$$\sigma_{\Delta m} = 1.46\,\sigma_{\Delta mq}$$

and $$\sigma_{\Delta s} = 0.65\,\sigma_{\Delta aq'}$$

The mass measurement error is slightly increased and the effective shear modulus measurement error is reduces; both in comparison to the intrinsic values for a Quartz sensor. Concurrent use of GaAs and Quartz SAW sensors appears to yield quite good results for simultaneous mass and effective shear modulus change measurements. The inventive approach of using more than one sensor, each having different material or material properties, was developed upon realization that the contribution of the shear modulus (stiffness) to the frequency response in a microporous material during gas adsorption was not negligible. This approach also means that other property measurements may be enhanced by relating the matrixed effect of multiple material properties to the frequency response.

Again referring to the use of the dual sensor structure described in FIG. 2, the stress in the film, caused by the adsorption of methanol into the micropores is calculated using Stoney's equation:

$$\langle \sigma_f \rangle = \frac{E_{si}}{6(1-\gamma_{si})}\frac{H}{2B}\frac{t_{si}^2}{Lh} \quad (20)$$

where:
$\sigma_f$ is the stress developed in the film,
$E_{si}$ is Young's modulus for silicon (148 Gpa),
$Y_{si}$ is the Poisson ratio for silicone (0.18),
H is the height of the measured beam deflection,
B is the path length (4.816 cm),
$t_{si}$ is the thickness of the silicone (150 $\mu$m),
L is the sample length (3,913 cm), and
h is the silica film thickness (900 Å).

The beam-bending technique gives an independent measurement of stress, which is used to calculate the stress and surface tension contribution to the SAW response.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A method for measuring the mass of adsorbent in a porous material at various pressures, comprising:

a) providing first and second acoustic sensors, each having different operating characteristics to provide different responses to identical inputs such that contributions of mass and effective modulus of the material to the responses of the sensors are separated;

b) applying identical material on a chosen surface of each of the first and second acoustic sensors, the applied material being the material to be measured;

c) placing the first and second acoustic sensors in a measurement environment;

d) providing adsorbent into the measurement environment at various pressures and measuring the responses of the first and second acoustic sensors at each pressure; and e) calculating the mass of adsorbent in the material based on the responses of the first and second acoustic sensors.

2. The method of claim 1, wherein the adsorbent is gas.

3. The method of claim 1, wherein the material is a thin-film.

4. The method of claim 1, wherein the first and second acoustic sensors are first and second SAW sensors.

5. The method of claim 1, wherein the responses being measured are frequency responses.

6. The method of claim 1, wherein the step of applying comprises applying thin-film material.

7. The method of claim 1, wherein the chosen surface of each of the first and second acoustic sensors is a top surface of each of the first and second acoustic sensors.

8. The method of claim 1, wherein the measurement environment is a chamber.

9. The method of claim 5, wherein the material to be measured comprises a thin-film material and the frequency responses of the first and second acoustic sensors is related to the mass and effective modulus by the following equation:

$$\begin{bmatrix} \Delta f_1 \\ \Delta f_2 \end{bmatrix} = \begin{bmatrix} -\frac{f_{o1}}{4}V_{R1}(R_{y1}+R_{z1}) & \frac{f_{o1}}{V_{R1}}R_{z1} \\ -\frac{f_{o2}}{4}V_{R2}(R_{y2}+R_{z2}) & \frac{f_{o1}}{V_{R2}}R_{z2} \end{bmatrix} \begin{bmatrix} \Delta m \\ \Delta s \end{bmatrix}$$

$$= S \begin{bmatrix} \Delta m \\ \Delta s \end{bmatrix}$$

where, $\Delta f_{1,2}$=the frequency shift of first or second sensor $f_{o1,o2}$=the frequency of oscillation of an unloaded first or second sensor $V_{R1,2}$=the velocity of the acoustic wave $R_{y1,2x1,2}=|V_{Ry1,2,z1,2}|^2/P_R$=the normalized surface particle velocity $\Delta m$=hp=the surface mass velocity $$\Delta s = \Delta\left(h\mu'\lambda' + \frac{\mu'}{\lambda'+2\mu'}\right) = \text{the effective shear}$$

modulus term (sometimes referred to as the stiffness)

$\mu'$=shear modulus of the isotropic thin-film h=thickness of the isotropic thin-film.

10. The method as in claim 1, wherein the first and second acoustic sensors each comprise a different piezoelectric material, the piezoelectric material being chosen to provide complementary information.

11. The method as in claim 4, wherein the first SAW sensor is quartz and the second SAW sensor is GaAs.

12. A device for measuring the mass of adsorbent in a porous material at various pressures, comprising:

a) a measurement environment adapted to receive the adsorbent under various pressures;

b) first and second acoustic sensors disposed within said measurement environment, said sensors each having a surface chosen for receiving an application of identical material, the applied material being the material to be measured;

c) a circuit for measuring the responses of said first and second acoustic sensors when loaded with the applied material at various pressures of the adsorbent; and d) said first and second acoustic sensors having different operating characteristics to provide different responses to identical inputs such that contributions of mass and effective modulus of the applied material to the responses of said sensors are separated.

13. The device of claim 12, wherein the adsorbent is gas.

14. The device of claim 12, wherein the material is a thin-film.

15. The device of claim 12, wherein said first and second acoustic sensors are first and second SAW sensors.

16. The device of claim 12, wherein the responses being measured are frequency responses.

17. The device of claim 12, wherein said applied material comprises thin-film material.

18. The device of claim 12, wherein said chosen surface of each of said first and second acoustic sensors is a top surface of each of said first and second acoustic sensors.

19. The device of claim 12, wherein said measurement environment is a chamber.

20. The device of claim 16, wherein the material to be measured comprises a thin-film material and the frequency responses of said first and second acoustic sensors are related to the mass and effective modulus by the following equation:

$$\begin{bmatrix} \Delta f_1 \\ \Delta f_2 \end{bmatrix} = \begin{bmatrix} -\frac{f_{o1}}{4}V_{R1}(R_{y1}+R_{z1}) & \frac{f_{o1}}{V_{R1}}R_{z1} \\ -\frac{f_{o2}}{4}V_{R2}(R_{y2}+R_{z2}) & \frac{f_{o1}}{V_{R2}}R_{z2} \end{bmatrix} \begin{bmatrix} \Delta m \\ \Delta s \end{bmatrix}$$

$$= S \begin{bmatrix} \Delta m \\ \Delta s \end{bmatrix}$$

where, $\Delta f_{1,2}$=the frequency shift of first or second sensor $f_{o1,o2}$=the frequency of oscillation of an unloaded first or second sensor $V_{R1,2}$=the velocity of the acoustic wave
$R_{y1,2x1,2}=|V_{Ry1,2,z1,2}|^2/P_R$=the normalized surface particle velocity
$\Delta m = h\rho$=the surface mass density $$\Delta s = \Delta\left(h\mu'\lambda' + \frac{\mu'}{\lambda' + 2\mu'}\right) = \text{the effective shear}$$

modulus term (sometimes referred to as the stiffness)

$\mu'$=shear modulus of the isotropic thin-film
h=thickness of the isotropic thin-film.

21. The device of claim 15, wherein said first SAW sensor is ST quartz.

22. The device of claim 15, wherein said second SAW sensor is GaAs.

23. The device of claim 12, wherein said first and second acoustic sensors each comprise a different piezoelectric material, said piezoelectric material being chosen to provide complementary information.

* * * * *